US012657741B2

(12) United States Patent　　　　　(10) Patent No.: US 12,657,741 B2
Guo et al.　　　　　　　　　　　　　　(45) Date of Patent: Jun. 16, 2026

(54) SYSTEMS AND METHODS FOR PREDICTING KEYPOINT MOVEMENT FOR MULTIPLE SURGICAL INSTRUMENTS USING SPATIAL-TEMPORAL GRAPH ATTENTION MODELING

(71) Applicant: INTUITIVE SURGICAL OPERATIONS, INC., Sunnyvale, CA (US)

(72) Inventors: Rui Guo, Suwanee, GA (US); Xi Liu, Peachtree Corners, GA (US); Ziheng Wang, Atlanta, GA (US); Anthony M. Jarc, Johns Creek, GA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 294 days.

(21) Appl. No.: 18/593,067

(22) Filed: Mar. 1, 2024

(65) Prior Publication Data

US 2024/0428428 A1　　Dec. 26, 2024

Related U.S. Application Data

(60) Provisional application No. 63/488,277, filed on Mar. 3, 2023.

(51) Int. Cl.
　G06T 7/246　　　(2017.01)
　A61B 34/20　　　(2016.01)
　G06T 7/73　　　(2017.01)
(52) U.S. Cl.
　CPC .............. G06T 7/248 (2017.01); A61B 34/20 (2016.02); G06T 7/73 (2017.01);
(Continued)

(58) Field of Classification Search
　CPC . G06T 7/248; G06T 7/73; G06T 2207/10016; G06T 2207/20072;
(Continued)

(56) References Cited

U.S. PATENT DOCUMENTS

2024/0252263 A1*　8/2024　Robu ............... A61B 1/000096

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

*Primary Examiner* — Stephen R Koziol
*Assistant Examiner* — Michael Kim Maiden
(74) *Attorney, Agent, or Firm* — Haynes & Boone, LLP.

(57)　　　　ABSTRACT

A method for predicting movement of a first plurality of keypoints of a first instrument comprises receiving, at a neural network model, a first location of the first plurality of keypoints and a first location of a second plurality of keypoints of a second instrument. The method further comprises determining a trajectory for the first and second pluralities of keypoints by: generating, using an attention model of the neural network model, a first and second tool-level graph indicating a spatial-temporal relationship between the first and second pluralities of keypoints, respectively; and generating a scene-level graph based on the tool-level graphs. The scene-level graph indicates a spatial-temporal relationship between the first and second pluralities of keypoints. The method further comprises generating an output image based on the determined trajectory. The output image includes an output location of the first and second pluralities of keypoints.

20 Claims, 13 Drawing Sheets

(52) U.S. Cl.
CPC ............... *G06T 2207/10016* (2013.01); *G06T*
*2207/20072* (2013.01); *G06T 2207/20084*
(2013.01); *G06T 2207/30004* (2013.01); *G06T*
*2207/30241* (2013.01)

(58) Field of Classification Search
CPC . G06T 2207/20084; G06T 2207/30004; A61B
34/20
See application file for complete search history.

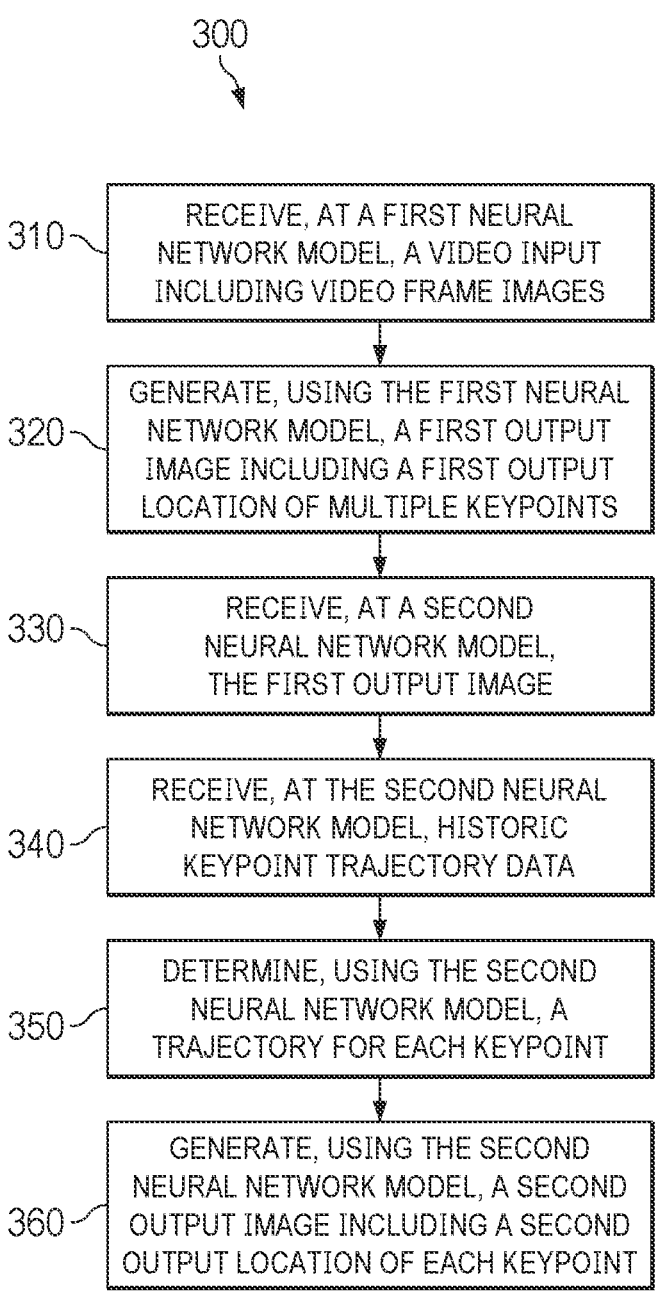

300

310 — RECEIVE, AT A FIRST NEURAL NETWORK MODEL, A VIDEO INPUT INCLUDING VIDEO FRAME IMAGES

320 — GENERATE, USING THE FIRST NEURAL NETWORK MODEL, A FIRST OUTPUT IMAGE INCLUDING A FIRST OUTPUT LOCATION OF MULTIPLE KEYPOINTS

330 — RECEIVE, AT A SECOND NEURAL NETWORK MODEL, THE FIRST OUTPUT IMAGE

340 — RECEIVE, AT THE SECOND NEURAL NETWORK MODEL, HISTORIC KEYPOINT TRAJECTORY DATA

350 — DETERMINE, USING THE SECOND NEURAL NETWORK MODEL, A TRAJECTORY FOR EACH KEYPOINT

360 — GENERATE, USING THE SECOND NEURAL NETWORK MODEL, A SECOND OUTPUT IMAGE INCLUDING A SECOND OUTPUT LOCATION OF EACH KEYPOINT

610 — GENERATE A KEYPOINT GRAPH BASED ON THE KEYPOINT LOCATIONS IN AN OUTPUT IMAGE RECEIVED FROM A SPATIAL NEURAL NETWORK MODEL

620 — GENERATE A VIRTUAL CENTROID BASED ON THE KEYPOINT GRAPH

630 — GENERATE A TOOL-LEVEL GRAPH USING THE VIRTUAL CENTROID

640 — GENERATE A SCENE-LEVEL GRAPH BASED ON THE TOOL LEVEL GRAPH

SYSTEMS AND METHODS FOR PREDICTING KEYPOINT MOVEMENT FOR MULTIPLE SURGICAL INSTRUMENTS USING SPATIAL-TEMPORAL GRAPH ATTENTION MODELING

CROSS-REFERENCE TO RELATED APPLICATIONS

This application claims priority to and the benefit of U.S. Provisional Application No. 63/488,277, filed Mar. 3, 2023, and entitled "Systems and Methods for Predicting Keypoint Movement for Multiple Surgical Instruments Using Spatial-Temporal Graph Attention Modeling," which is incorporated by reference herein in its entirety.

FIELD

Examples described herein relate generally to machine learning models and neural networks, and more specifically, systems and methods for predicting keypoint movement for multiple surgical instruments using spatial-temporal graph attention modeling.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Robust visual tracking for multiple agents empowers many autonomous applications. Despite the importance, attempts in building reliable trackers are suffering due to the high complexity in de-coupling spatial-temporal correlations using the neural network. For some other applications, such as robotic assisted surgery, tracking the pose of one or more instruments benefits from a high-fidelity model. Compared to a general Multiple Object Tracking (MOT) scenario, surgical instruments used during surgery usually interact with each other. The dynamic modeling of instrument interactions for surgery-specific actions such as dissection, retraction, and suturing directly affects the performance of tracking.

Based on modeling the social behavior of crowd pedestrians, researchers introduced the social long short-term memory network ("LSTM") as a kernel that describes the dynamics of pedestrians' interactions, where the latent motions represented with the hidden states of LSTMs are shared by the mechanism of "social-pooling." Advanced in the social pooling design, individual pedestrians are not treated as isolated entities, but are grouped together at the pooling based on defined "neighborhood" relations. Soft attention is also utilized to establish the relative influence among the pedestrians. The attention model calculates a weight matrix that assigned unequal importance to the neighboring pedestrians. It increases the flexibility of the model to understand the crowd behavior based on the spatial interactions. However, social-LSTM models each pedestrian equally using a LSTM. It may not be applicable to a complex entity with an obvious hierarchical structure.

SUMMARY

Various features may improve keypoint movement prediction for multiple surgical instruments. The following presents a simplified summary of various examples described herein and is not intended to identify key or critical elements or to delineate the scope of the claims.

Consistent with some examples, a method for predicting movement of a first plurality of keypoints of a first surgical instrument is provided. The method includes receiving, at a neural network model, a first location of each keypoint of the first plurality of keypoints of the first surgical instrument and a first location of each keypoint of a second plurality of keypoints of a second surgical instrument. The method further includes determining, using the neural network model, a trajectory for each keypoint of the first plurality of keypoints and the second plurality of keypoints. The trajectories are determined by generating, using an attention model of the neural network model, a first tool-level graph indicating a spatial-temporal relationship between the first plurality of keypoints of the first surgical instrument. The trajectories are further determined by generating, using the attention model of the neural network model, a second tool-level graph indicating a spatial-temporal relationship between the second plurality of keypoints of the second surgical instrument. The trajectories are further determined by generating a scene-level graph based on the first and second tool-level graphs. The scene-level graph indicates a spatial-temporal relationship between the first plurality of keypoints and the second plurality of keypoints. The method further includes generating, using the neural network model, an output image based on the determined trajectory for each keypoint of the first plurality of keypoints and the second plurality of keypoints. The output image includes an output location of each keypoint of the first plurality of keypoints annotated on an output image of the first surgical instrument. The output image further includes an output location of each keypoint of the second plurality of keypoints annotated on an output image of the second surgical instrument.

Consistent with other examples, a system for predicting movement of a first plurality of keypoints of a first surgical instrument is provided. The system includes a memory configured to store a neural network model. The system further includes a processor coupled to the memory. The processor is configured to receive, at the neural network model, a first location of each keypoint of the first plurality of keypoints of the first surgical instrument and a first location of each keypoint of a second plurality of keypoints of a second surgical instrument. The processor is further configured to determine, using the neural network model, a trajectory for each keypoint of the first plurality of keypoints and the second plurality of keypoints. The trajectories are determined by generating, using an attention model of the neural network model, a first tool-level graph indicating a spatial-temporal relationship between the first plurality of keypoints of the first surgical instrument. The trajectories are further determined by generating, using the attention model of the neural network model, a second tool-level graph indicating a spatial-temporal relationship between the second plurality of keypoints of the second surgical instrument. The trajectories are further determined by generating a scene-level graph based on the first and second tool-level graphs. The scene-level graph indicates a spatial-temporal relationship between the first plurality of keypoints and the second plurality of keypoints. The processor is further configured to generate, using the neural network model, an output image based on the determined trajectory for each keypoint of the first plurality of keypoints and the second plurality of keypoints. The output image includes an output location of each keypoint of the first plurality of keypoints annotated on an output image of the first surgical instrument.

The output image further includes an output location of each keypoint of the second plurality of keypoints annotated on an output image of the second surgical instrument.

Consistent with other examples, a non-transitory machine-readable medium having stored thereon machine-readable instructions executable to cause a machine to perform operations that predict movement of a first plurality of keypoints of a first surgical instrument is provided. The operations include receiving, at a neural network model a first location of each keypoint of the first plurality of keypoints of the first surgical instrument and a first location of each keypoint of a second plurality of keypoints of a second surgical instrument. The operations further includes determining, using the neural network model, a trajectory for each keypoint of the first plurality of keypoints and the second plurality of keypoints. The trajectories are determined by generating, using an attention model of the neural network model, a first tool-level graph indicating a spatial-temporal relationship between the first plurality of keypoints of the first surgical instrument. The trajectories are further determined by generating, using the attention model of the neural network model, a second tool-level graph indicating a spatial-temporal relationship between the second plurality of keypoints of the second surgical instrument. The trajectories are further determined by generating a scene-level graph based on the first and second tool-level graphs. The scene-level graph indicates a spatial-temporal relationship between the first plurality of keypoints and the second plurality of keypoints. The operations further include generating, using the neural network model, an output image based on the determined trajectory for each keypoint of the first plurality of keypoints and the second plurality of keypoints. The output image includes an output location of each keypoint of the first plurality of keypoints annotated on an output image of the first surgical instrument. The output image further includes an output location of each keypoint of the second plurality of keypoints annotated on an output image of the second surgical instrument.

Other examples include corresponding computer systems, apparatus, and computer programs recorded on one or more computer storage devices, each configured to perform the actions of any one or more methods described below.

It is to be understood that both the foregoing general description and the following detailed description are illustrative and explanatory in nature and are intended to provide an understanding of the various examples described herein without limiting the scope of the various examples described herein. In that regard, additional aspects, features, and advantages of the various examples described herein will be apparent to one skilled in the art from the following detailed description.

BRIEF DESCRIPTIONS OF THE DRAWINGS

FIG. 3 illustrates a method for detecting one or more keypoints using a spatial neural network model and a temporal neural network model according to some examples.

Figure 1:
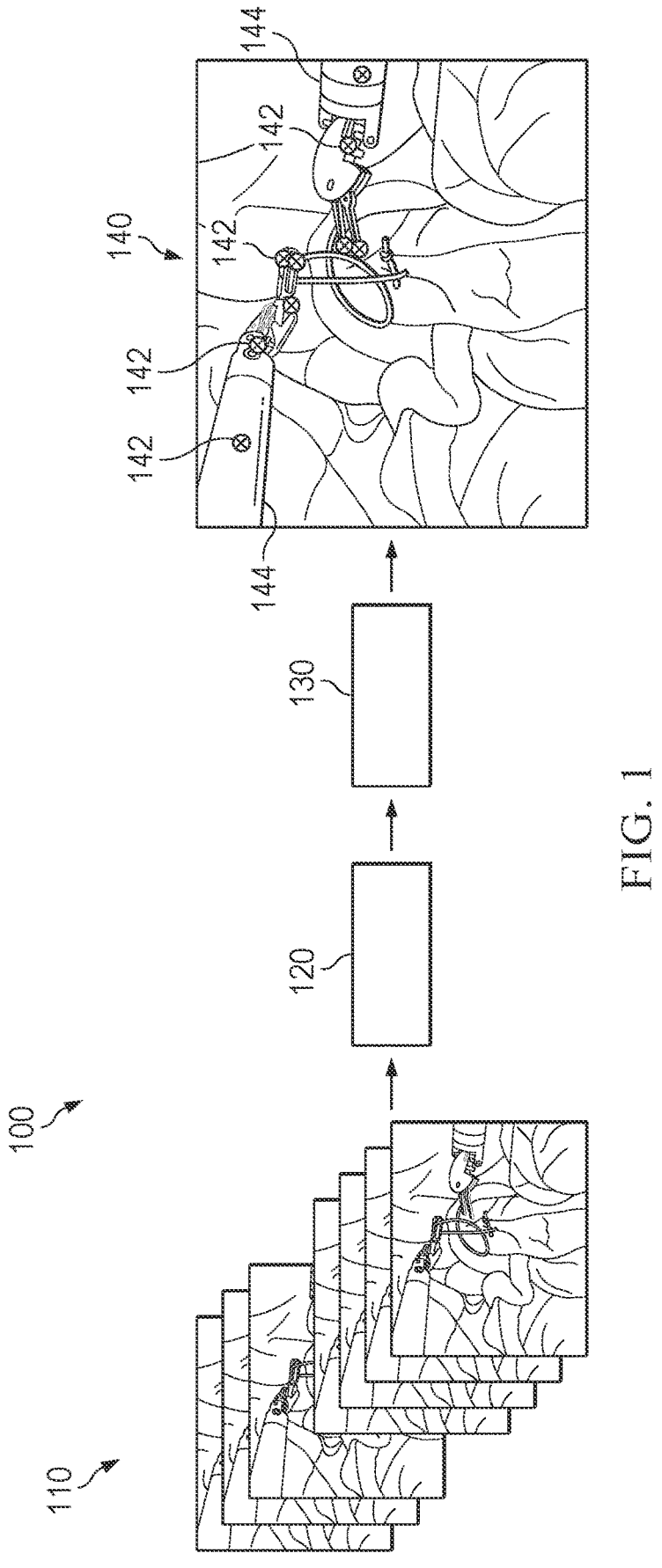
FIG. 1 illustrates a keypoint detection workflow including a spatial neural network model and a temporal neural network model according to some examples.

Various examples described herein and their advantages are described in the detailed description that follows. It should be appreciated that like reference numerals are used to identify like elements illustrated in one or more of the figures for purposes of illustrating but not limiting the various examples described herein.

DETAILED DESCRIPTION

The theory of graph neural networks inspires advanced modeling using graph representations for un-structured data. The examples described herein illustrate a Spatial-Temporal Graph hierarchy, where the spatial and temporal interactions among surgical instruments are encoded, respectively. The spatial interactions at one time-step are captured by the graph attention scheme, which models over all the surgical instruments in the clinical operation. After assigning a different importance on keypoints, an extra LSTM is used to capture the temporal correlations of interactions between surgical instruments. By aggregating all the spatial-and-temporal interactions among all the keypoints and instrument entities, the future trajectories are generated by a sequence-to-sequence (seq2seq) translation. To model the diverse motion patterns, the intra-instrument keypoints are modeled in the lower level and the inter-instrument interactions are also modeled by defining root nodes and connecting them in higher level graph topology.

In some examples, besides modeling the multiple instruments interactions, object association is another aspect that may additionally or alternatively affect the tracking performance. Conventional models utilize trajectories only to understand the dynamics of tracked objects in the past, but one directional temporal encoding ignores the future movement. This results in inconsistent tracking association due to the imperfection of localization error accumulated over time. Tracking-by-prediction is a sophisticated scheme that bridges the gap. Instead of temporal correlation from historic traces, the tracked objects in the next frame are associated with targets by considering their predicted short- and long-term motions. The bi-directional continuity enforces the smoothness and correction of the tracking associations in potentially ambiguous scenarios.

The following description will further describe surgical instrument tracking-by-prediction with an inductive hierarchical spatial-temporal graph network. In some examples, a graph hierarchy is generated to represent the spatial-temporal complexity embedded in the multiple surgical instrument tracking problem. The model explicitly extends the graph to predict trajectories of multiple surgical tools in the surgery. The model explicitly encodes the spatial-temporal correlation with emphasis on the instruments' interaction. Additionally or alternatively, the tracking may be re-framed by aggregating the predictions to mitigate any data association inaccuracy.

Localizing instrument keypoints and tool parts in video-assisted surgeries is an attractive and open problem in computer vision. A working algorithm may be useful in computer-aided interventions in the operating room with, for example, a robotically-assisted surgical system. Knowing the location of tool parts may help virtually augment visual faculty of surgeons, assess skills of novice surgeons, and increase autonomy of surgical robots. Additionally, knowing the location of tool parts may assist with generating haptic feedback, evaluating user skills, and automating endoscopic motion based on the tracked location of the tools.

FIG. 1 illustrates a keypoint detection workflow 100. The workflow 100 illustrates an exemplary process by which one or more keypoints of a surgical instrument or tool may be detected. Video input 110 may be received by a spatial neural network model 120. The spatial neural network model 120 may be a convolutional neural network model or any other spatial neural network model. The video input 110 may include one or more individual video frame images. In some examples, the video frame images encompass a video recording of a previously performed surgical procedure. In some examples, the video input 110 includes video-only surgical data. After the spatial neural network model 120 processes the video input 110, an output of the spatial neural network model 120 may be received by a temporal neural network model 130. The temporal neural network model 130 may be a recurrent neural network model or any other temporal neural network model. After the temporal neural network model 130 processes the output of the spatial neural network model 120, the temporal neural network model 130 may output an image 140. The image 140 may be one of the images in the video input 110 and may include additional icons or annotations 142 illustrating the location of one or more keypoints of one or more surgical instruments 144 included in the image 140. In some examples, the temporal neural network model 130 may output multiple images, which may correspond to each of the video frame images included in the video input 110. Each out the output images from the temporal neural network model 130 may include icons or annotations illustrating the location of the keypoint(s) of the surgical instrument(s) included in the output image(s). In some examples, the temporal neural network model 130 outputs the locations of the keypoint(s) of the surgical instrument(s) in the format of trajectories such as graphical arrows indicating a direction of motion. The trajectories may illustrate how the locations of the keypoint(s) changed over the course of the surgical procedure.

Figure 2:
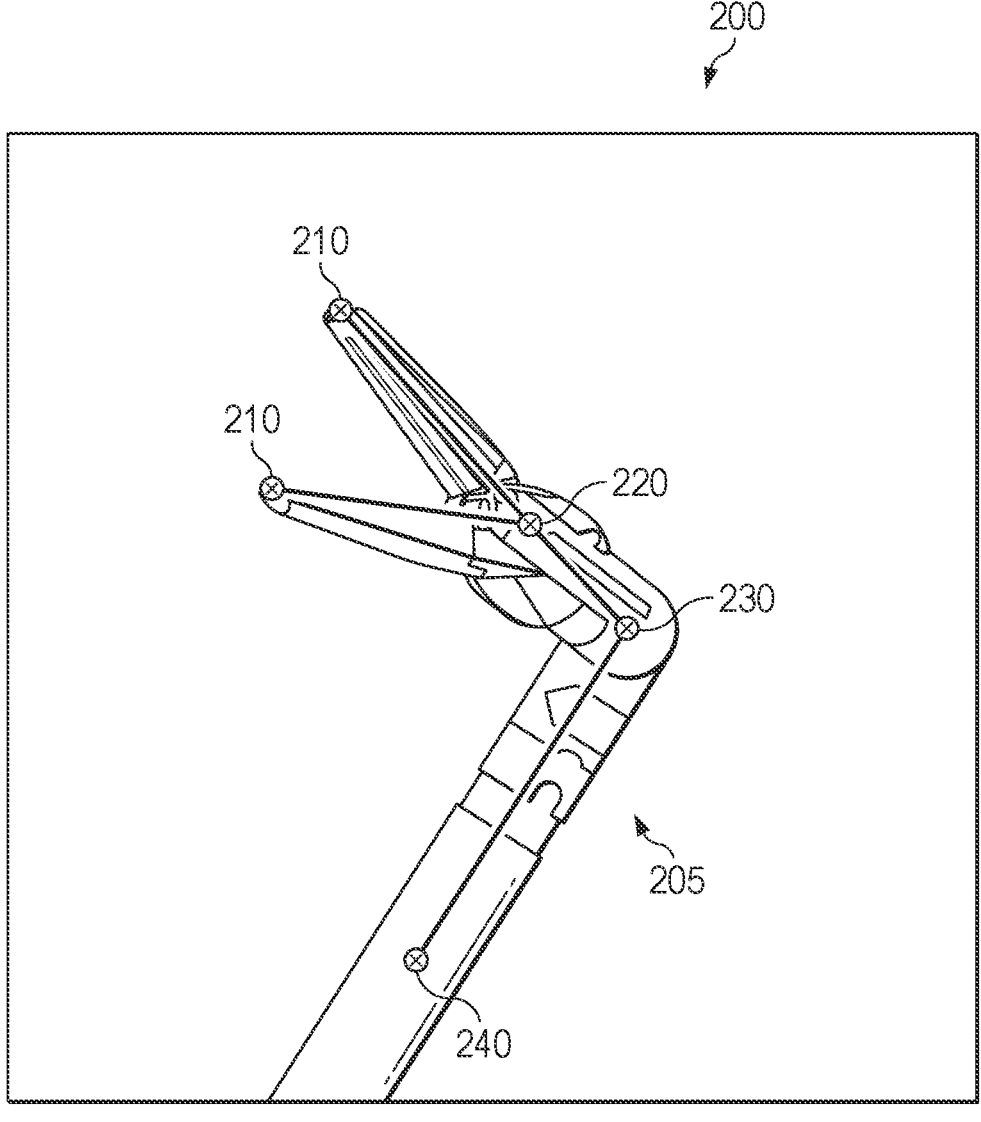
FIG. 2 illustrates an image including icons identifying one or more keypoints on a surgical instrument according to some examples.

FIG. 2 illustrates an image 200 including icons or annotations identifying keypoints on a surgical instrument 205. Several different surgical instruments or variations of surgical instruments may be used during a surgical procedure. For example, the surgical instrument 205 may have two prongs at its distal tip (e.g., a grasping instrument) or one or more prongs at its distal tip (e.g., a biopsy instrument). To accommodate for various surgical instruments, a predetermined keypoint or set of keypoints is identified based on the type of surgical instrument being used during the surgical procedure. Each keypoint identifies a location of a corresponding landmark of the surgical instrument 205, such as keypoints 210 at the distal tip of the surgical instrument 205, a keypoint 220 at the clevis of the surgical instrument 205, a keypoint 230 at the clevis shaft of the surgical instrument 205, and a keypoint 240 at the shaft end of the surgical instrument 205.

FIG. 3 illustrates an example of a method 300 for detecting and tracking one or more keypoints using a spatial neural network model (e.g., the neural network model 120) and a temporal neural network model (e.g., the neural network model 130) in accordance with some aspects of the present disclosure. The method 300 is illustrated as a set of operations or processes 310-360. The processes 310-360 may be performed in the same or in a different order than the order shown in FIG. 3. One or more of the illustrated processes may be omitted in some examples of the method 300. Additionally, one or more processes that are not expressly illustrated in the flowchart may be included before, after, in between, or as part of the illustrated processes. In some examples, one or more of the processes of the flowchart may be implemented, at least in part, by a control system (e.g., the control system 812 of FIG. 8) executing code stored on non-transitory, tangible, machine-readable media that when run by one or more processors (e.g., the one or more processors of the control system 812) may cause the one or more processors to perform one or more of the processes.

Figure 4:
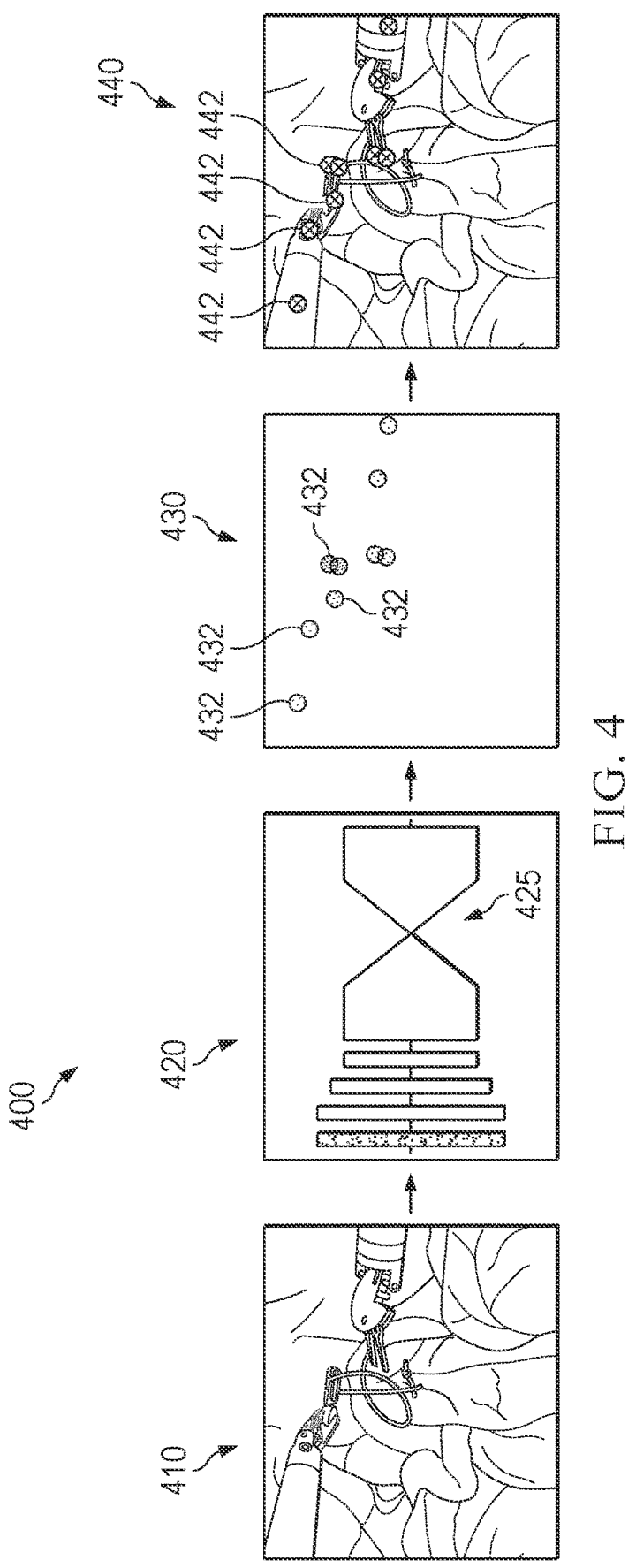
FIG. 4 illustrates a partial keypoint detection workflow including a spatial neural network model according to some examples.
Figure 5A:
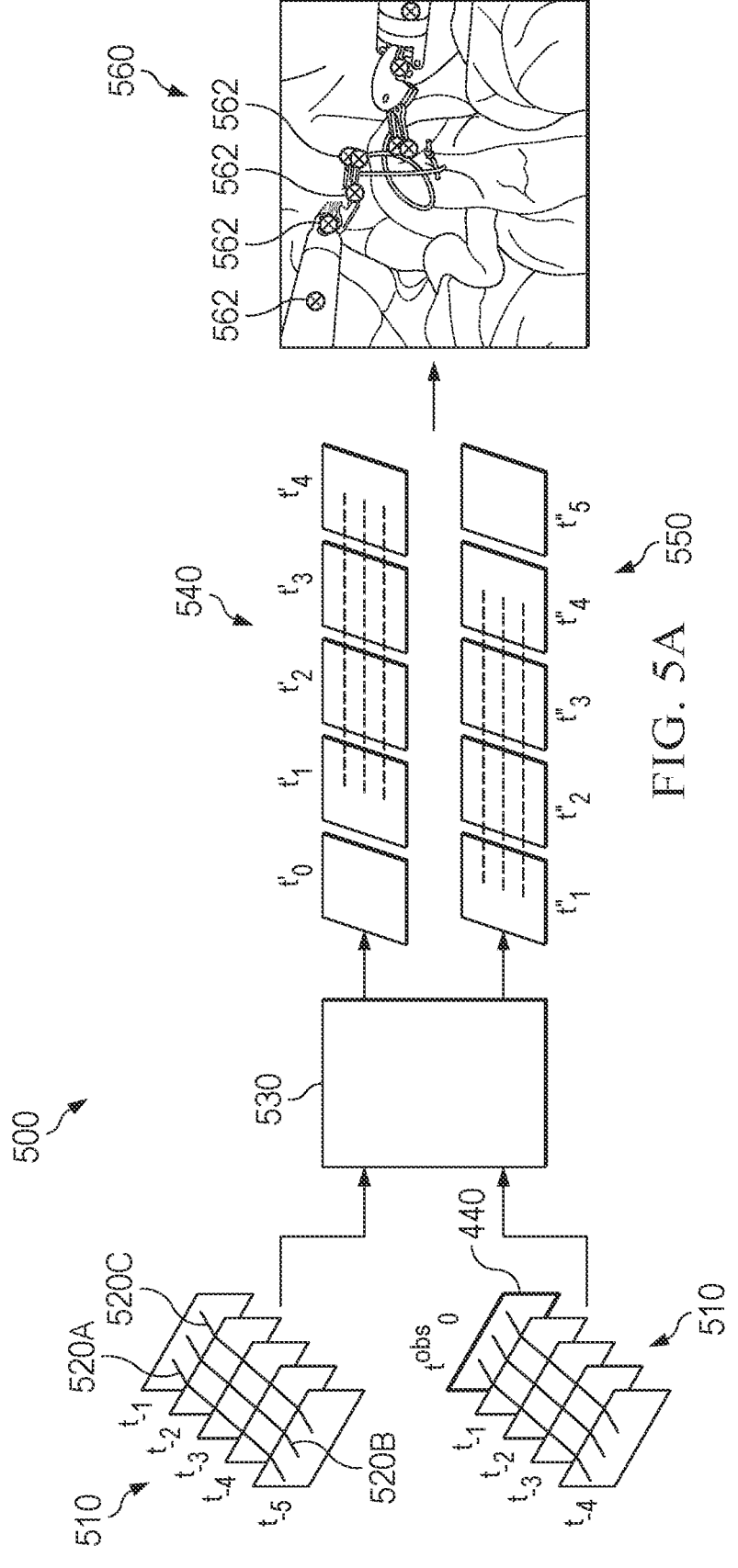
FIG. 5A illustrates a partial keypoint detection workflow including a temporal neural network model according to some examples.

The method 300 will be described with continuing reference to FIGS. 4 and 5. FIG. 4 illustrates a partial keypoint detection workflow 400 including a spatial neural network model 420 (e.g., the spatial neural network model 120) model. FIG. 5A illustrates a partial keypoint detection workflow 500 including a temporal neural network model (e.g., the temporal neural network model 130) according to some examples.

At a process 310, video input 410 (e.g., the video input 110) is received at the spatial neural network model 420. As discussed above, the video input 410 may include one or more video frame images. In some examples, the spatial neural network model 420 may include an hourglass module 425. For example, a multiple-layered neural network may be used as a spatial information encoder.

In some examples, the spatial neural network model 420 may include a cascaded hourglass network structure. Scale invariant capability may be needed in the spatial information encoding for keypoint localization. To enhance such a capability, multiple hourglass networks may be stacked together in some examples to hierarchically process the video input 410. The stacked feature maps may be aggregated to incorporate multiple-scale spatial modeling. At the last layer of the spatial neural network model 420, the output feature vector may be regressed to infer the location of the heatmap. There is a duplicated output used to infer the tags of the parts at the same time. Then, clustering may be conducted using the estimated tags and distance metric to group the individual gaussian maps into an instrument.

The spatial neural network model 420 may output a heatmap 430. A heatmap, such as the heatmap 430, may include a graphical representation of data with values, such as locations of one or more keypoints, depicted by color. The heatmap 430 includes one or more icons 432 that illustrate estimated locations of the keypoints for the surgical instrument(s). In some examples, the keypoints are estimated using a pre-defined Gaussian distribution. The spatial neural network model 420 may learn a regression model that maps the input video frame image 410 into the heatmap 430. The icons 432 may vary in brightness depending on the confidence with which each icon represents an accurate location of a keypoint. For example, the pixel value of an icon may increase in brightness as the confidence with which the icon represents an accurate location of a keypoint increases.

In some examples, the spatial neural network model 420 may additionally or alternatively output an output image 440. The output image 440 includes icons 442 that indicate an output location of one or more keypoints of one or more surgical instruments. The output image 440 may be generated based on the heatmap 430. For example, the spatial neural network model 420 may utilize the estimated keypoint locations in the heatmap 430 to identify a final location of the keypoint(s). The spatial neural network model 420 may then cause the icons 442 to be overlaid on the output image 440 to identify the final locations of the keypoint(s).

With reference to FIG. 3, at a process 330, the output image 440 may be received at a temporal neural network model 530 (e.g., the temporal neural network model 130). In some examples, the heatmap may additionally or alternatively be received at the temporal neural network model 530 in addition to or in place of the output image 440. At a process 340, historic keypoint trajectory data 510 may also be received at the temporal neural network model 530. The historic keypoint trajectory data 510 includes a historic trajectory for each keypoint. Historic trajectories 520A, 520B, 520C illustrate exemplary trajectories over time, which may be illustrated as trajectory lines mapped across several video frame images over time.

Keypoint localization techniques that use only a spatial neural network model may result in an output image with keypoint locations that may not accurately match the actual location of the keypoint(s) of the surgical instrument(s). False positive keypoint identifications and/or failing to detect a keypoint may occur. The keypoint localization process of only a spatial neural network model may be improved by interconnecting the spatial neural network model with a temporal neural network model to refine the results output by the spatial neural network model. In some examples, utilizing the temporal encoding of keypoint sequences may improve the performance of keypoint localization. The temporal neural network model 530 may learn from historic keypoint trajectories (e.g., the historic trajectories 520A, 520B, 520C) and may determine the future dynamics of the tracked keypoint(s). Given the historic trajectories of the keypoint(s), the temporal neural network model 530 may efficiently learn the dynamics of the keypoint(s) and may determine the future locations of the keypoint(s). In one example, the temporal neural network model 530 may be a layered neural network using concatenated long short-term memory as the basic units. The temporal neural network model 530 may be trained off-line using ground-truth trajectories of the surgical instrument.

In some examples, the output image 440 generated by the spatial neural network model 420 may be received by the temporal neural network model 530 along with the historic trajectories 510. The temporal neural network model 530 may then iteratively match the current observation of the keypoint locations in the current output image 440 to the historic trajectories 510. In one exemplary process, the data association and iterative matching may be performed in the following manner. It is to be understood that the algorithms described below and/or the order in which the algorithms below are presented may be varied depending on specific circumstances in which the temporal neural network model 530 is used.

For historical traces $T_{-n}$, $T_{1-n}$, . . . $T_{-1}$, the predictor P may be applied to process these n-step information and predict the next m-step possible locations where the object is going to move.

$$\hat{T}_0, \hat{T}_1, \dots, \hat{T}_{m-1} = P(T_{-n}, T_{1-n}, \dots, T_{-1})$$

The current observation Obo (from the output image 440 of the spatial neural network model 420) may be assigned to associate with the historical trajectories 510. Again, the same predictor P may be utilized to process n-step information with associated observation and predict the next m-step possible locations of the object:

$$\hat{T}_1^h, \hat{T}_2^h, \dots, \hat{T}_m^h = P(T_{1-n}, T_{2-n}, \dots, T_{-1}, Ob_0)$$

The prediction 540, which is a prediction based only on the historic trajectories 510, may include a segment overlapped with the prediction 550, which is a prediction based on the combination of the historic trajectories 510 and the output image 440, which is from time t=1 to t=m−1. The prediction segment 540 (eq (1)) may be defined as $\hat{T}$ and the prediction segment 550 (eq (2)) is defined as $\hat{T}^h$. The final association may be determined by minimizing the metrics over all the predictions:

$$\min_h D\left(\hat{T}, \hat{T}^h\right)$$

where, D is a defined distance metric to calculate the distance between $\hat{T}$ and $\hat{T}^h$. One example of distance metrics is a Mahalanobis distance. Based on the optimization results, the prediction with the lowest distance error may be chosen for associating the locations of the keypoint(s) in the output image 440 with the historic trajectories 510. Using the above process, the temporal neural network model 530 may determine a future trajectory for each keypoint at a process 350.

Figure 5B:
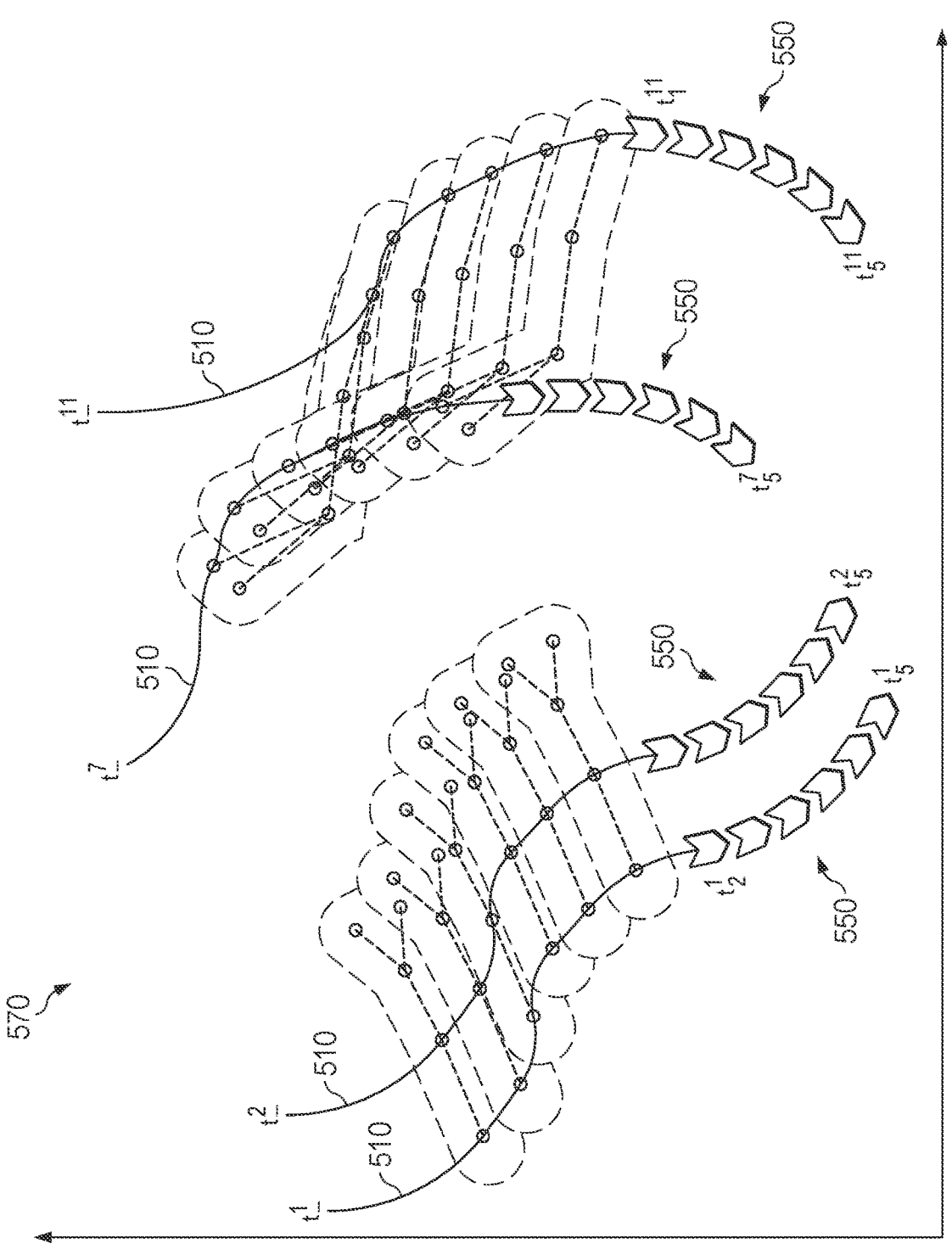
FIG. 5B illustrates a historical trajectory graph and a predicted trajectory graph output by the temporal neural network model of FIG. 5A according to some examples.

In some examples, when the input includes frames n=5, the output generates frames m=5. The predictions 540 may include predictions using only the historic trajectories 510. The predictions 550 may include predictions with one association of the current locations of the keypoint(s) in the output image 440 with the historic trajectories 510. The predictions 540, 550 have four frames overlapped, as shown in FIG. 5A. In some examples, as shown in FIG. 5B, the temporal neural network model 530 may generate the historical trajectories 510 and the predictions 550 in a graph 570. The graph 570 illustrates the historical trajectories 510 and the predictions 550 in a non-linear manner.

Figure 5C:
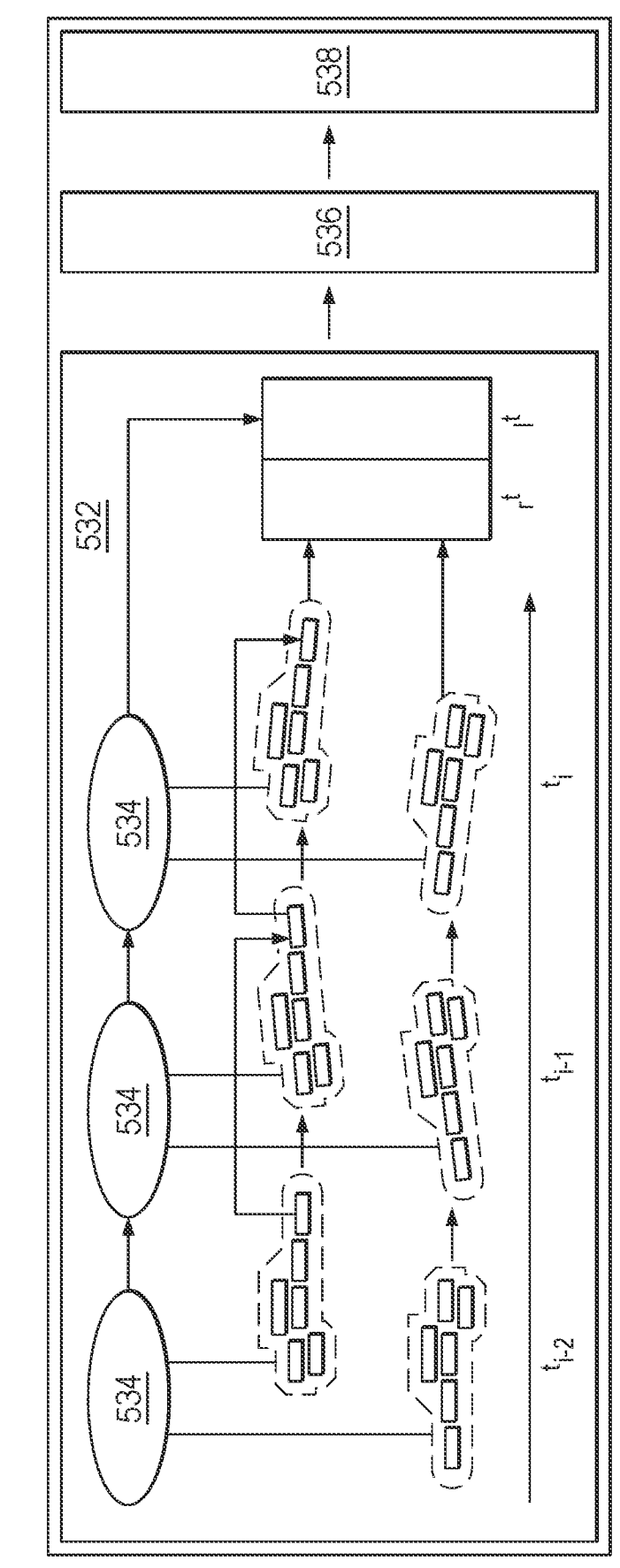
FIG. 5C illustrates a structure of the temporal neural network model of FIG. 5A according to some examples.

FIG. 5C illustrates an example structure of the temporal neural network model 530. In some examples, the temporal neural network model 530 may be a spatial-temporal graph attention network ("STGAT"). The STGAT may include a processing unit that takes a graphical input, such as the graphical historical trajectories 510 in FIG. 5B, and encodes the information into numerical feature vectors. The feature vectors may be decoded into a representation in a target domain of the task to recognize, classify, and predict the objective (e.g., trajectories of the keypoint(s)). The STGAT may include various implementations that vary in how the layered structure of the temporal neural network model 530 is formatted. For example, the temporal neural network model 530 may include one or more alternative neural processing units, such as a pooling processing unit, a convolution processing unit, a regression mapping processing unit, or a concatenation processing unit. FIG. 5C illustrates one exemplary structure of the temporal neural network model 530.

The temporal neural network model 530 of FIG. 5C includes a recurrent processing unit 532. The recurrent processing unit may receive a sequential input and extract temporal correlations from the sequential input along a temporal dimension. The sequential input may include detected locations of one or more keypoints of a surgical instrument (e.g., the detected locations identified in the output image 440 output by the spatial neural network model 420). Additionally or alternatively, the sequential input may include the historical trajectory 510 of one or more keypoints of the surgical instrument. The recurrent processing unit 532 may be structured as a chain of long short-term memory.

The temporal neural network model 530 may also include one or more attention models 534. In some examples, the attention model(s) may be part of the recurrent processing unit 532. The attention model(s) 534 may assign a weight and/or reorganize the weightings applied to the sequential input data received by the recurrent processing unit 532. The attention model(s) 534 may efficiently select the most contributive input data to formalize the representation/feature. For example, the attention model(s) 534 may determine which keypoint locations in the received input data most closely correspond to a historical trajectory of each keypoint. The attention model(s) 534 may be applied in both a spatial dimension and a temporal dimension.

The temporal neural network model 530 may also include an encoder-decoder module 536. The STGAT may be composed of an encoder-decoder structured neural network. In an encoding stage, the recurrent processing unit 532 may take the original input vector and project it into latent space to conduct a spatial-temporal correlation decoupling. In a decoding stage, the hidden states representation may be projected back to the original space and regressed to generate a result vector corresponding to labels, coordinates, or other targeted information.

The temporal neural network model 530 may also include a predictor module 538. In some examples, the graph attention model 534 may process the encoded sequential input data in graph format. The attention model 534 may extract the significant factors that contribute to the final representation of the predicted trajectories. Using the scene-level graph as input, the interaction of multiple surgical instruments represented by grouped graph vertices are efficiently explored and processed by the graph attention model 534. Based on the modeled dynamics from the recurrent processing unit 532, the predictor module 538 may determine the future movement and trajectory of the keypoint(s) of the surgical instrument.

Figure 6:
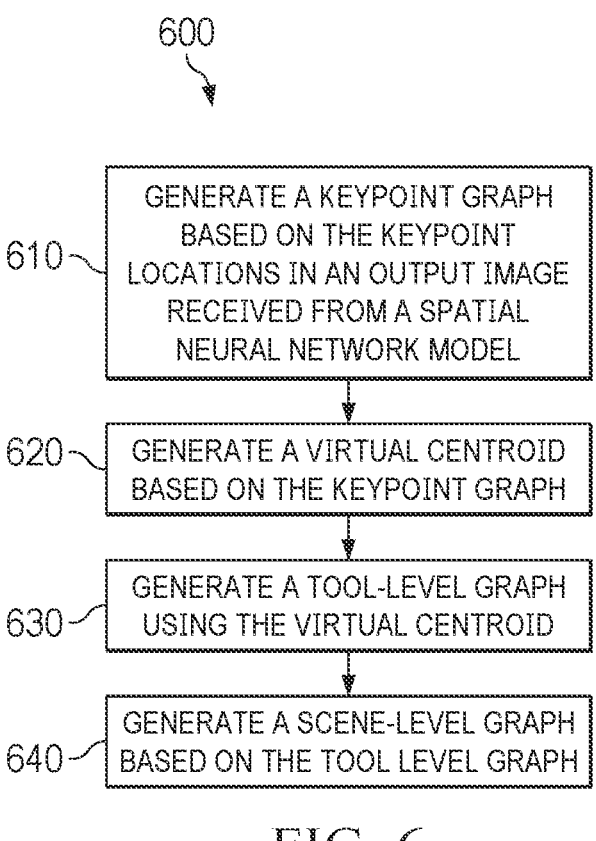
FIG. 6 illustrates an optional method for determining the trajectory of each keypoint according to some examples.

FIG. 6 illustrates an example of a method 600 for determining the trajectory for each keypoint using the temporal neural network model 530 in accordance with some aspects of the present disclosure. The method 600 illustrates one exemplary method of performing the process 350 of the method 300. The method 600 is illustrated as a set of operations or processes 610-640. The processes 610-640 may be performed in the same or in a different order than the order shown in FIG. 6. One or more of the illustrated processes may be omitted in some examples of the method 600. Additionally, one or more processes that are not expressly illustrated in the flowchart may be included before, after, in between, or as part of the illustrated processes. In some examples, one or more of the processes of the flowchart may be implemented, at least in part, by a control system (e.g., the control system 812 of FIG. 8) executing code stored on non-transitory, tangible, machine-readable media that when run by one or more processors (e.g., the one or more processors of the control system 812) may cause the one or more processors to perform one or more of the processes.

Figure 7A:
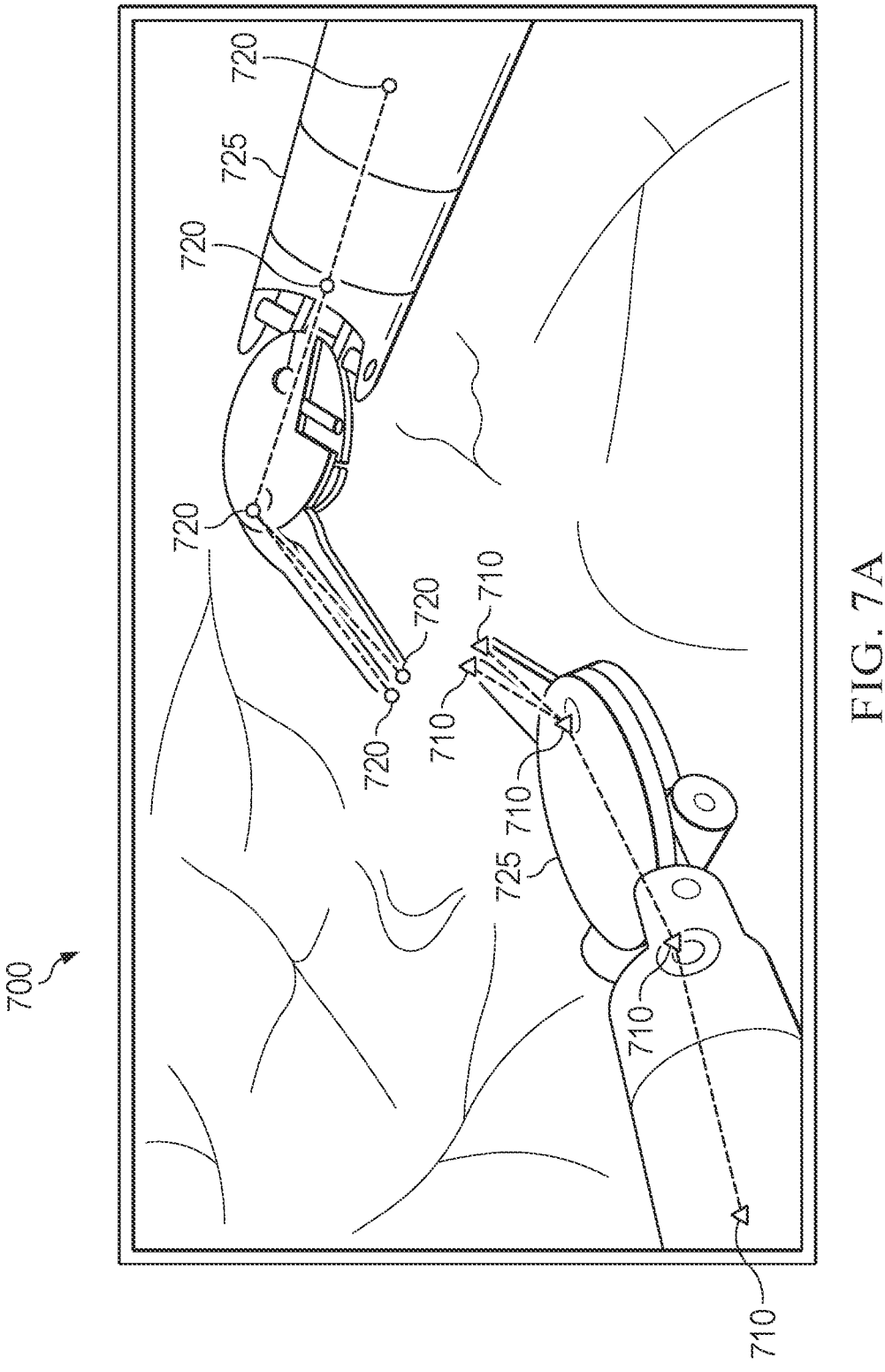
FIG. 7A illustrates an output image of a spatial neural network model, the output image including icons identifying one or more keypoints on a surgical instrument according to some examples.

The method 600 will be described with continuing reference to FIGS. 5A-5C and 7A-7D. FIG. 7A illustrates an output image 700 (e.g., the output image 440) of a spatial neural network model (e.g., the spatial neural network model 420). The output image 700 includes icons 710 identifying one or more keypoint locations on a surgical instrument 715. The output image 700 may also include icons 720 identifying one or more keypoint locations on a surgical instrument 725. Two surgical instruments 715, 725 are shown in the output image 700. The following discussion will be made with reference to two surgical instruments displayed in the output image 700. This is for exemplary purposes only, and the output image 700 may include one, three, or any other number of surgical instruments in other examples.

Figure 7B:
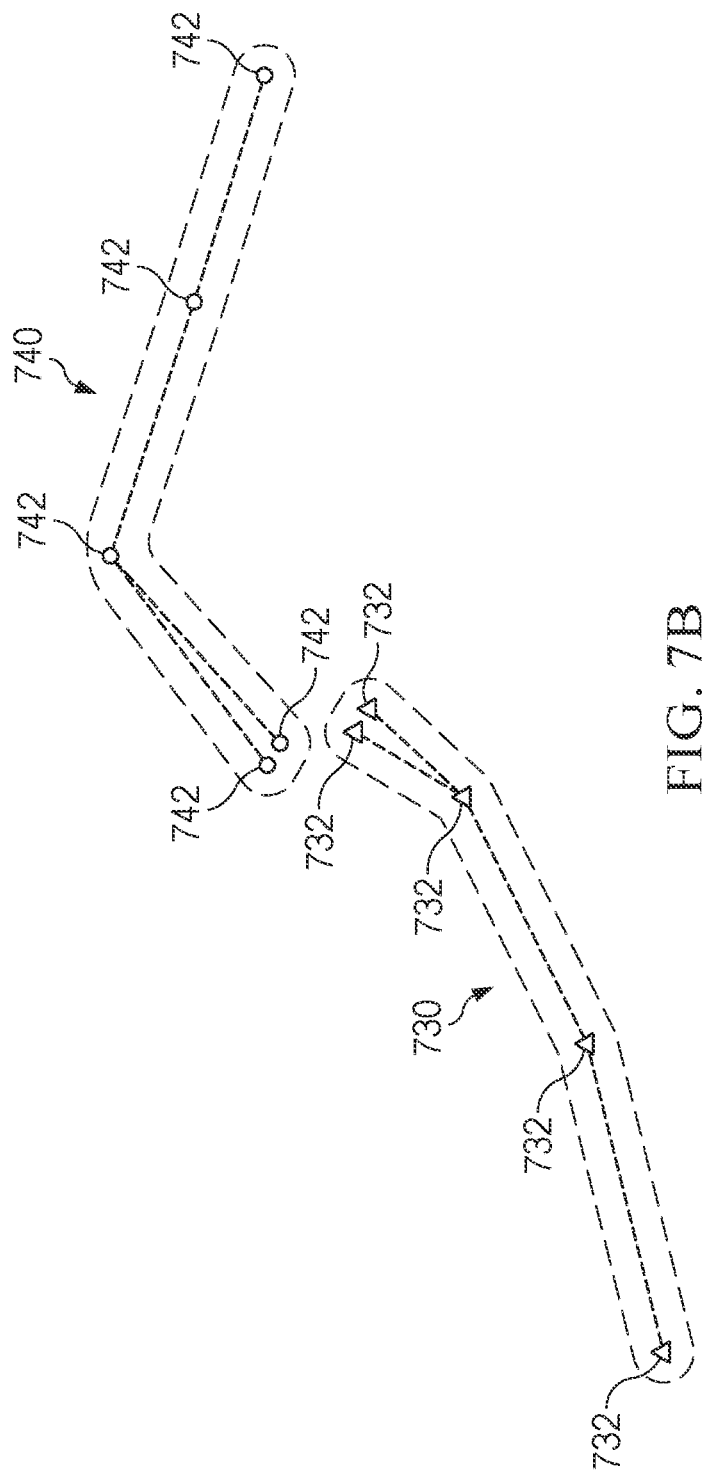
FIG. 7B illustrates a keypoint graph corresponding to keypoints of a surgical instrument according to some examples.
Figure 7C:
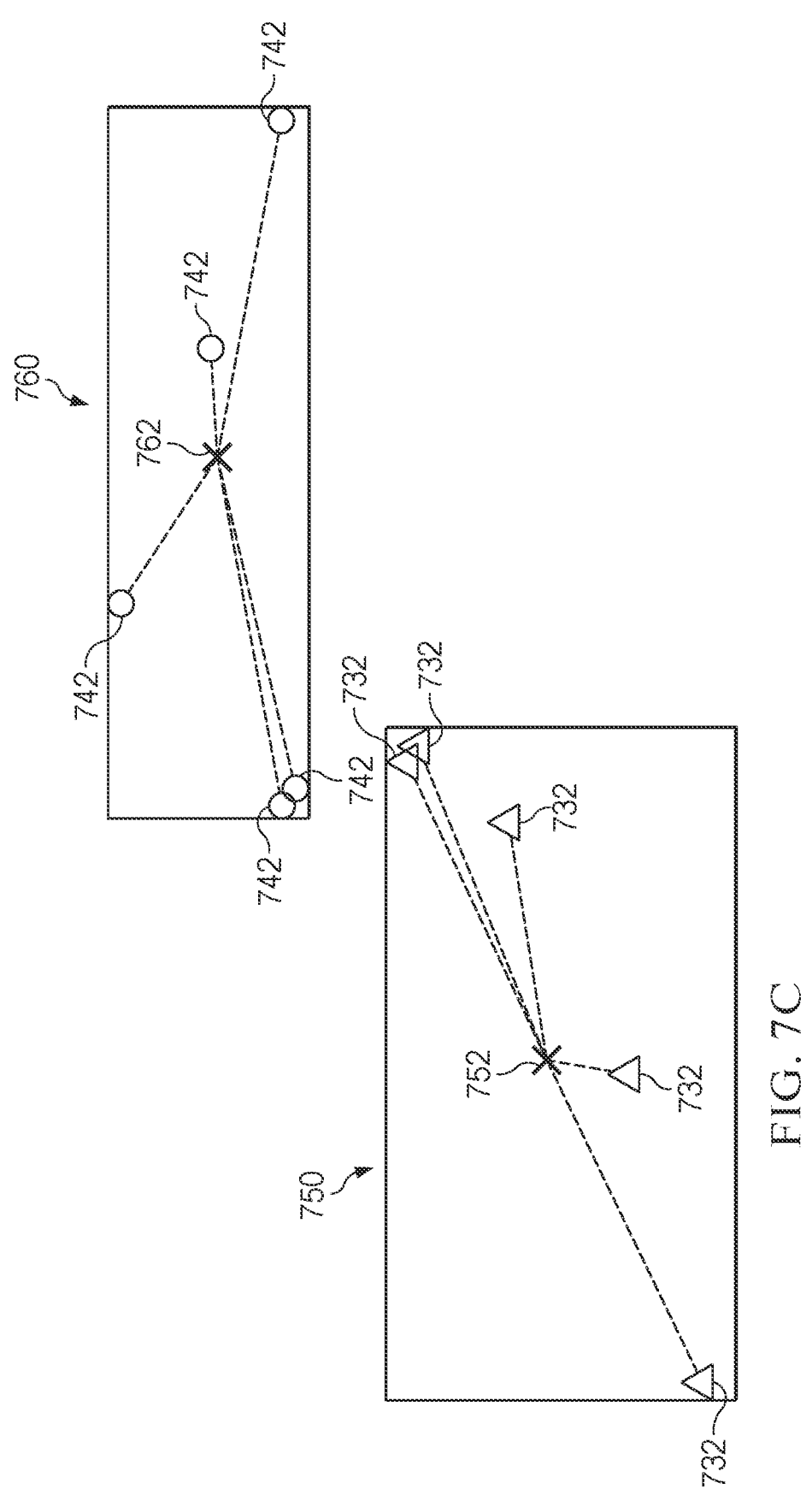
FIG. 7C illustrates a tool-level graph including keypoints of a surgical instrument according to some examples.
Figure 7D:
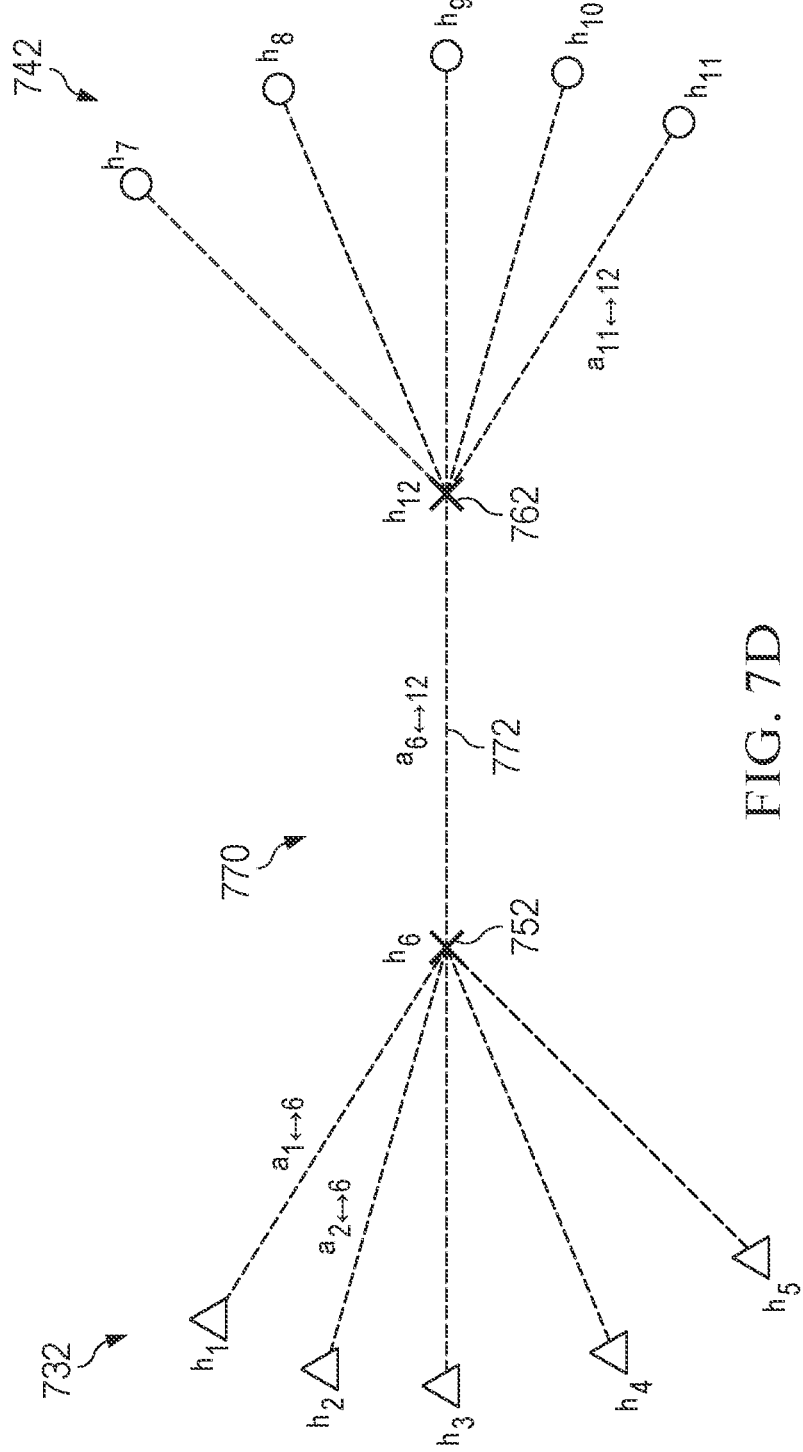
FIG. 7D illustrates a scene-level graph including keypoints of a surgical instrument according to some examples.

FIG. 7B illustrates a keypoint graph 730 corresponding to one or more keypoint locations 732 with respect to the surgical instrument 715. The keypoint locations 732 correspond to the location of the icons 710 in the output image 700. FIG. 7B also illustrates a keypoint graph 740 corresponding to one or more keypoint locations 742 with respect to the surgical instrument 725. The keypoint locations 742 correspond to the location of the icons 720 in the output image 700. FIG. 7C illustrates a tool-level graph 750 corresponding to the keypoint locations 732 with respect to the surgical instrument 715. The tool-level graph 750 includes a virtual centroid 752. FIG. 7C also illustrates a tool-level graph 760 corresponding to the keypoint locations 742 with respect to the surgical instrument 725. The tool-level graph 760 includes a virtual centroid 762. FIG. 7D illustrates a scene-level graph 770 corresponding to the tool-level graph 750 and the tool-level graph 760. The scene-level graph 770 includes a connection 772 between the virtual centroid 752 and the virtual centroid 762.

At a process 610, a keypoint graph (e.g., the keypoint graph 730 and/or the keypoint graph 740) is generated based on the keypoint locations identified in the output image 440 received from the spatial neural network model 420. In some examples, there are five landmarks on each surgical instrument that are identified as keypoint locations in the output image 440. Any other number of keypoint locations may be identified. Additionally or alternatively, the location coordinates of each keypoint may be determined based on kinematic data corresponding to each surgical instrument received from a robot-assisted medical system (e.g., the robot-assisted medical system 800 of FIG. 8.).

At a process 620, a virtual centroid (e.g., the virtual centroid 752 and/or the virtual centroid 762) is generated based on the keypoint graph 730 and/or the keypoint graph 740. In some examples, a virtual centroid is generated for each surgical instrument that is included in the output image 700. The virtual centroid is the geometric center of the keypoint locations of a surgical instrument. For example, the virtual centroid 752 is the geometric center of the keypoint locations 732 of the surgical instrument 715. The virtual centroid 762 is the geometric center of the keypoint locations 742 of the surgical instrument 725.

At a process 630, a tool-level graph (e.g., the tool-level graph 750 and/or the tool-level graph 760) is generated using the virtual centroid. For example, each keypoint location 732 is connected to the virtual centroid 752 to generate the tool-level graph 750. The tool-level graph 750 provides a graphical representation of the spatial-temporal relationship between the keypoint locations 732. The tool-level graph 760 provides a graphical representation of the spatial-temporal relationship between the keypoint locations 742. Each keypoint location 742 is connected to the virtual centroid 762 to generate the tool-level graph 760. The keypoint locations 732 and the virtual centroid 752 are vertexes in the tool-level graph 750. The connections between the keypoint locations 732 and the virtual centroid 752 are defined as edges in the tool-level graph 750. The keypoint locations 742 and the virtual centroid 762 are vertexes in the tool-level graph 760. The connections between the keypoint locations 742 and the virtual centroid 762 are defined as edges in the tool-level graph 760. In some examples, the keypoint locations 732 may only be connected to the virtual centroid 752 and not to each other. In some examples, the keypoint locations 742 may only be connected to the virtual centroid 762 and not to each other.

At a process 640, a scene-level graph (e.g., the scene-level graph 770) is generated based on the tool-level graph(s). The scene-level graph 770 provides a graphical representation of the spatial-temporal relationship between the keypoint locations for all of the surgical instruments identified in the output image 700 (e.g., the keypoint locations 732 and the keypoint locations 742). In examples when multiple surgical instruments are used during the surgical procedure, the scene-level graph connects the tool-level graph for each surgical instrument together. For example, the virtual centroids of each tool-level graph may be connected. As shown in the example of FIG. 7D, the virtual centroid 752 is connected to the virtual centroid 762 via a connection 772. In this example, only the virtual centroids 752, 762 are adjacent neighbors in the scene-level graph 770. The keypoint locations from different surgical instruments remain independent of each other and unconnected from each other in the scene-level graph 770. In examples when only one surgical instrument is illustrated in the output image 700, the tool-level graph and the scene-level graph may be the same graph.

In some examples, the temporal neural network model 530 may determine the trajectory for each keypoint based on the scene-level graph 770. In some examples, the location(s) of each vertex of the scene-level graph 770 (e.g., the keypoint locations 732, 742 and the virtual centroids 752, 762) and any extended feature vectors, such as histogram color, texture representation of the small neighboring area, and other learned features could be concatenated together to generate a representation of the vertices. In some examples, a distance measurement of each edge of the scene-level graph 770 (e.g., the connections between the keypoint locations 732 and the virtual centroid 752 and/or the connections between the keypoint locations 742 and the virtual centroid 762) may be represented by one or more of the feature vectors discussed above.

After merging the current locations of the keypoint(s) in the output image 440 with the historic trajectories 510, a smoothness filter may be applied to the predicted trajectories 550 to further reduce any noise from the raw detection. At a process 360, the temporal neural network model 530 may generate a refined output image 560, which includes icons 562 illustrating a refined location of the keypoint(s) of the surgical instrument in that particular video frame image. In some examples, the refined output image 560 may be generated based on the scene-level graph 770. The temporal neural network model 530 may output multiple refined output images corresponding to each video frame image in the video input 110 to illustrate the changing locations of the keypoint(s) over the course of the surgical procedure. In some examples, the refined output image 560 may be displayed on a display system, such as the display system 810. In some examples, the predicted trajectories 550 may be displayed on a display system, such as the display system 810.

In some examples, if a particular video frame image does not include one or more of the keypoints (e.g., if a part of the surgical instrument is occluded from view), the trajectory of the missing keypoint may be interpolated. The missing keypoint may be interpolated based on the application of the smoothness filter.

One or more of the keypoint detection processes described above may be used to evaluate a performance of the surgical procedure based on the refined output image(s) 560 corresponding to each video frame image of the video input 110. For example, the locations of the keypoint(s) may be used to calculate and/or evaluate one or more objective performance indicators (OPI's). The OPI's may help evaluate how effectively and/or how efficiently a surgeon performed the surgical procedure. For example, a Time OPI may track the amount of time each surgical instrument was active and the amount of time each surgical instrument was inactive during the surgical procedure.

An Instrument Movement OPI may track one or more of: a speed of instrument movement (median and/or mean); a smoothness of instrument movement (e.g., normalized speed and/or speed peaks); a range of motion of the instrument; a distance of the instrument from a camera (e.g., an endoscopic camera); an economy of instrument motion (e.g., the total distance travelled by the instrument); and bimanual dexterity (e.g., proportion of instrument distances, difference in instrument distances). A Wrist and Grip Metric OPI may track instrument wrist and instrument grip angles (mean, median, total) and/or instrument wrist angular velocity.

One or more of the keypoint detection processes described above may additionally or alternatively be used to determine whether the surgical instrument will exceed its range of motion based on the determined trajectory 550 of each keypoint. In some examples, if a determination is made that the surgical instrument will exceed its range of motion, a warning may be generated to indicate that the surgical instrument will exceed its range of motion. The warning may be audible, haptic, textual, or any combination thereof. The determinations may be made by one or more processors of a control system (e.g., the control system 812).

One or more of the keypoint detection processes described above may additionally or alternatively be used to determine whether the surgical instrument will collide with another surgical instrument based on the determined trajectory 550 of each keypoint. In some examples, if a determination is made that the surgical instrument will collide with another surgical instrument, a warning may be generated to indicate that the surgical instrument will exceed its range of motion. The warning may be audible, haptic, textual, or any combination thereof. The determinations may be made by one or more processors of a control system (e.g., the control system 812).

In some examples, the scene-level graph 770 discussed above may represent one or more surgical instruments in a surgical procedure to efficiently determine and/or display the spatial-temporal relationship between the keypoint locations in the video input 110. The attention model(s) 534 in the temporal neural network model 530 may uniquely distinguish and model non-linear interactions between multiple surgical instruments in a surgical environment.

Figure 8:
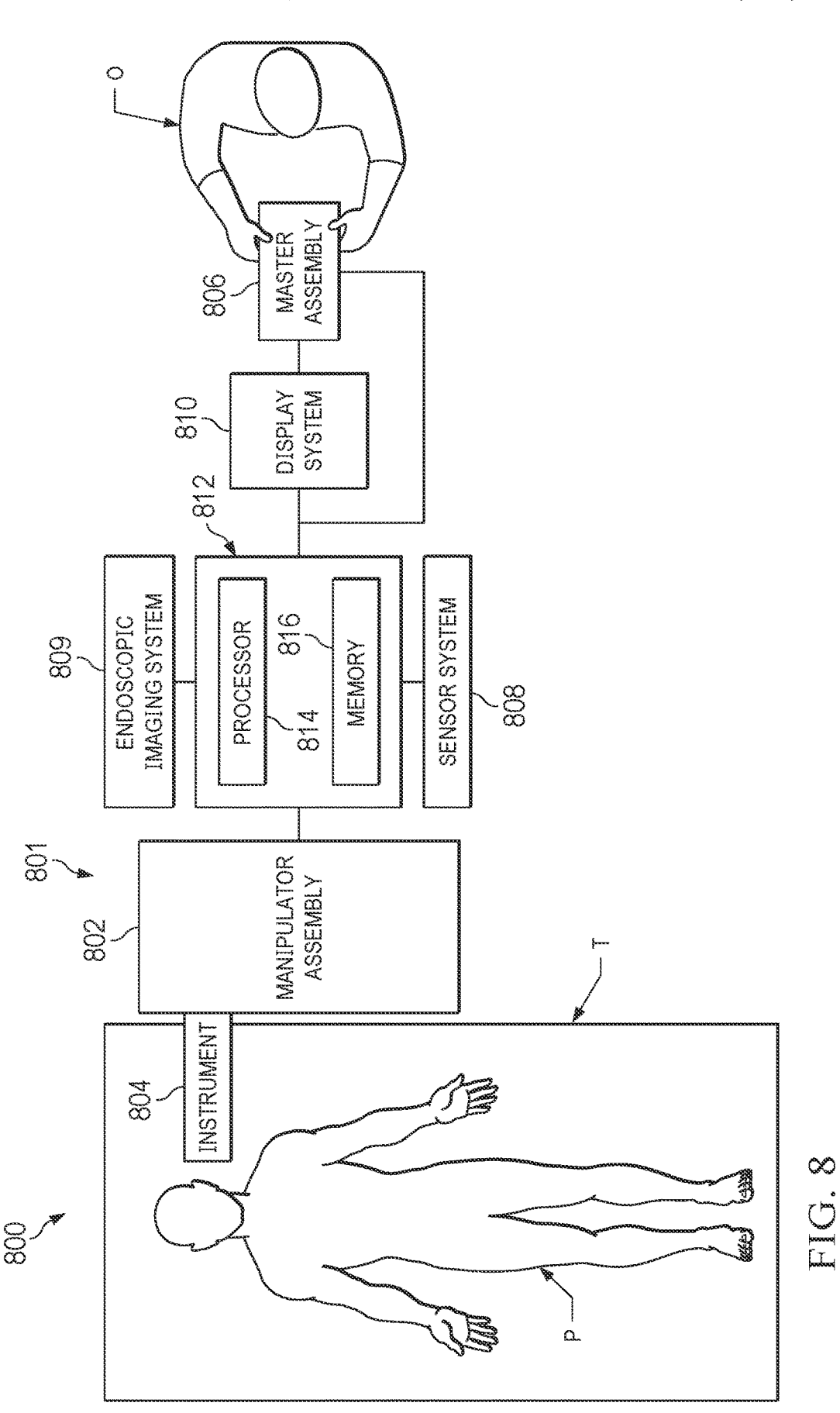
FIG. 8 illustrates a simplified diagram of a robotic or teleoperated medical system according to some examples according to some examples.

In some examples, the keypoint detection techniques of this disclosure, such as those discussed in relation to method 300 of FIG. 3 and the method 600 of FIG. 6, may be used in an image-guided medical procedure performed with a robot-assisted medical system as shown in FIG. 8. FIG. 8 illustrates a robot-assisted medical system 800. The robot-assisted medical system 800 generally includes a manipulator assembly 802 for operating a medical instrument system 804 (including, for example, an elongate device) in performing various procedures on a patient P positioned on a table T in a surgical environment 801. The manipulator assembly 802 may be robot-assisted, non-assisted, or a hybrid robot-assisted and non-assisted assembly with select degrees of freedom of motion that may be motorized and/or robot-assisted and select degrees of freedom of motion that may be non-motorized and/or non-assisted. A master assembly 806, which may be inside or outside of the surgical environment 801, generally includes one or more control devices for controlling manipulator assembly 802. Manipulator assembly 802 supports medical instrument system 804 and may optionally include a plurality of actuators or motors that drive inputs on medical instrument system 804 in response to commands from a control system 812. The actuators may optionally include drive systems that when coupled to medical instrument system 804 may advance medical instrument system 804 into a naturally or surgically created anatomic orifice. Other drive systems may move the distal end of medical instrument system 804 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument system 804 for grasping tissue in the jaws of a biopsy device and/or the like.

Robot-assisted medical system 800 also includes a display system 810 for displaying an image or representation of the surgical site and medical instrument system 804 generated by a sensor system 808 and/or an endoscopic imaging system 809. Display system 810 and master assembly 806 may be oriented so operator O can control medical instrument system 804 and master assembly 806 with the perception of telepresence.

In some examples, medical instrument system 804 may include components for use in surgery, biopsy, ablation, illumination, irrigation, or suction. Optionally medical instrument system 804, together with sensor system 808 may be used to gather (e.g., measure) a set of data points corresponding to locations within anatomical passageways of a patient, such as patient P. In some examples, medical instrument system 804 may include components of the imaging system 809, which may include an imaging scope assembly or imaging instrument that records a concurrent or real-time image of a surgical site and provides the image to the operator or operator O through the display system 810. The concurrent image may be, for example, a two or three-dimensional image captured by an imaging instrument positioned within the surgical site. In some examples, the imaging system components that may be integrally or removably coupled to medical instrument system 804. However, in some examples, a separate endoscope, attached to a separate manipulator assembly may be used with medical instrument system 804 to image the surgical site. The imaging system 809 may be implemented as hardware, firmware, software or a combination thereof which interact with or are otherwise executed by one or more computer processors, which may include the processors of the control system 812.

The sensor system 808 may include a position/location sensor system (e.g., an electromagnetic (EM) sensor system) and/or a shape sensor system (e.g., an optical fiber shape sensor system) for determining the position, orientation, speed, velocity, pose, and/or shape of the medical instrument system 804. In some examples, the sensor system 808 includes a shape sensor. The shape sensor may include an optical fiber extending within and aligned with the medical instrument system 804 (e.g., an elongate device). In one example, the optical fiber has a diameter of approximately 200 μm. In other examples, the dimensions may be larger or smaller. The optical fiber of the shape sensor forms a fiber optic bend sensor for determining the shape of the elongate device. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in some examples may employ other suitable strain sensing techniques, such as Rayleigh scattering, Raman scattering, Brillouin scattering, and Fluorescence scattering. In some examples, the shape of the catheter may be determined using other techniques. For example, a history of the distal end pose of the elongate device can be used to reconstruct the shape of the elongate device over the interval of time.

Robot-assisted medical system 800 may also include control system 812. Control system 812 includes at least one memory 816 and at least one computer processor 814 for effecting control between medical instrument system 804, master assembly 806, sensor system 808, endoscopic imaging system 809, and display system 810. Control system 812 also includes programmed instructions (e.g., a non-transitory machine-readable medium storing the instructions) to implement some or all of the methods described in accordance with aspects disclosed herein, including instructions for providing information to display system 810.

Control system 812 may optionally further include a virtual visualization system to provide navigation assistance to operator O when controlling medical instrument system 804 during an image-guided surgical procedure. Virtual navigation using the virtual visualization system may be based upon reference to an acquired preoperative or intraoperative dataset of anatomical passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

The singular forms "a", "an", and "the" are intended to include the plural forms as well, unless the context indicates otherwise. And the terms "comprises," "comprising," "includes," "has," and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. Components described as coupled may be directly or indirectly communicatively coupled. The auxiliary verb "may" likewise implies that a feature, step, operation, element, or component is optional.

In the description, specific details have been set forth describing some examples. Numerous specific details are set forth in order to provide a thorough understanding of the examples. It will be apparent, however, to one skilled in the art that some examples may be practiced without some or all of these specific details. The specific examples disclosed herein are meant to be illustrative but not limiting. One skilled in the art may realize other elements that, although not specifically described here, are within the scope and the spirit of this disclosure.

Elements described in detail with reference to one example, implementation, or application optionally may be included, whenever practical, in other examples, implementations, or applications in which they are not specifically shown or described. For example, if an element is described in detail with reference to one example and is not described with reference to a second example, the element may nevertheless be claimed as included in the second example. Thus, to avoid unnecessary repetition in the following description, one or more elements shown and described in association with one example, implementation, or application may be incorporated into other examples, implementations, or aspects unless specifically described otherwise, unless the one or more elements would make an example or implementation non-functional, or unless two or more of the elements provide conflicting functions.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative example can be used or omitted as applicable from other illustrative examples. For the sake of brevity, the numerous iterations of these combinations will not be described separately. For simplicity, in some instances the same reference numbers are used throughout the drawings to refer to the same or like parts.

The systems and methods described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like. Although some of the examples described herein refer to surgical procedures or instruments, or medical procedures and medical instruments, the techniques disclosed apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

Further, although some of the examples presented in this disclosure discuss robotic-assisted systems or remotely operable systems, the techniques disclosed are also applicable to computer-assisted systems that are directly and manually moved by operators, in part or in whole.

Additionally, one or more elements in examples of this disclosure may be implemented in software to execute on a processor of a computer system such as a control processing system. When implemented in software, the elements of the examples of the present disclosure are essentially the code segments to perform the necessary tasks. The program or code segments can be stored in a processor readable storage medium (e.g., a non-transitory storage medium) or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit, a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller" or "control system", are analogous.

Note that the processes and displays presented may not inherently be related to any particular computer or other apparatus, and various systems may be used with programs in accordance with the teachings herein. The required structure for a variety of the systems discussed above will appear as elements in the claims. In addition, the examples of the present disclosure are not described with reference to any particular programming language. It will be appreciated that a variety of programming languages may be used to implement the teachings of the present disclosure as described herein.

While certain example examples of the present disclosure have been described and shown in the accompanying drawings, it is to be understood that such examples are merely illustrative of and not restrictive to the broad disclosed concepts, and that the examples of the present disclosure not be limited to the specific constructions and arrangements shown and described, since various other modifications may occur to those ordinarily skilled in the art.

What is claimed is:

1. A method for predicting movement of a first plurality of keypoints of a first surgical instrument, the method comprising:

receiving, at a neural network model:
a first location of each keypoint of the first plurality of keypoints of the first surgical instrument; and
a first location of each keypoint of a second plurality of keypoints of a second surgical instrument;
determining, using the neural network model, a trajectory for each keypoint of the first plurality of keypoints and the second plurality of keypoints by:
generating, using an attention model of the neural network model, a first tool-level graph indicating a spatial-temporal relationship between the first plurality of keypoints of the first surgical instrument;
generating, using the attention model of the neural network model, a second tool-level graph indicating a spatial-temporal relationship between the second plurality of keypoints of the second surgical instrument; and
generating a scene-level graph based on the first and second tool-level graphs, the scene-level graph indicating a spatial-temporal relationship between the first plurality of keypoints and the second plurality of keypoints; and
generating, using the neural network model, an output image based on the determined trajectory for each keypoint of the first plurality of keypoints and the second plurality of keypoints, the output image including:
an output location of each keypoint of the first plurality of keypoints annotated on an output image of the first surgical instrument; and
an output location of each keypoint of the second plurality of keypoints annotated on an output image of the second surgical instrument.

2. The method of claim 1, wherein the first location of each keypoint of the first plurality of keypoints is received at the neural network model as a first sequential input, wherein the first location of each keypoint of the second plurality of keypoints is received at the neural network model as a second sequential input.

3. The method of claim 2, wherein determining the trajectory for each keypoint of the first plurality of keypoints and the second plurality of keypoints further includes:

extracting, using the neural network model, a first temporal correlation between each keypoint of the first plurality of keypoints along a temporal dimension of the attention model; and
extracting, using the neural network model, a second temporal correlation between each keypoint of the second plurality of keypoints along the temporal dimension of the attention model.

4. The method of claim 1, further comprising determining, using the attention model, an interaction between the first surgical instrument and the second surgical instrument based on the scene-level graph.

5. The method of claim 1, wherein determining the trajectory for each keypoint of the first plurality of keypoints and the second plurality of keypoints further includes:

generating a first keypoint graph corresponding to the first plurality of keypoints; and
generating a second keypoint graph corresponding to the second plurality of keypoints.

6. The method of claim 5, wherein determining the trajectory for each keypoint of the first plurality of keypoints and the second plurality of keypoints further includes:

generating a first virtual centroid based on the first keypoint graph, the first virtual centroid defining a geometric center of the first plurality of keypoints; and
generating a second virtual centroid based on the second keypoint graph, the second virtual centroid defining a geometric center of the second plurality of keypoints.

7. The method of claim 6, wherein the first tool-level graph is generated based on the first virtual centroid, and wherein the second tool-level graph is generated based on the second virtual centroid.

8. The method of claim 1, wherein generating the first tool-level graph includes assigning a weight, using the attention model, to each keypoint of the first plurality of keypoints.

9. The method of claim 8, wherein the weight is assigned in a spatial dimension of the attention model or in a temporal dimension of the attention model.

10. The method of claim 1, wherein generating the output image includes determining, using the attention model, which output location for each keypoint in the first plurality of keypoints in the first output image most closely corresponds to a historical trajectory of each keypoint in the first plurality of keypoints.

11. A system for predicting movement of a first plurality of keypoints of a first surgical instrument, the system comprising:

a memory configured to store a neural network model; and
a processor coupled to the memory, the processor configured to:
receive, at the neural network model:
a first location of each keypoint of the first plurality of keypoints of the first surgical instrument; and
a first location of each keypoint of a second plurality of keypoints of a second surgical instrument;
determine, using the neural network model, a trajectory for each keypoint of the first plurality of keypoints and the second plurality of keypoints by:
generating, using an attention model of the neural network model, a first tool-level graph indicating a spatial-temporal relationship between the first plurality of keypoints of the first surgical instrument;
generating, using the attention model of the neural network model, a second tool-level graph indicating a spatial-temporal relationship between the second plurality of keypoints of the second surgical instrument; and
generating a scene-level graph based on the first and second tool-level graphs, the scene-level graph indicating a spatial-temporal relationship between the first plurality of keypoints and the second plurality of keypoints; and
generate, using the neural network model, an output image based on the determined trajectory for each keypoint of the first plurality of keypoints and the second plurality of keypoints, the output image including:

an output location of each keypoint of the first plurality of keypoints annotated on an output image of the first surgical instrument; and an output location of each keypoint of the second plurality of keypoints annotated on an output image of the second surgical instrument.

12. The system of claim 11, wherein determining the trajectory for each keypoint of the first plurality of keypoints and the second plurality of keypoints further includes:

extracting, using the neural network model, a first temporal correlation between each keypoint of the first plurality of keypoints along a temporal dimension of the attention model; and extracting, using the neural network model, a second temporal correlation between each keypoint of the second plurality of keypoints along the temporal dimension of the attention model.

13. The system of claim 11, wherein determining the trajectory for each keypoint of the first plurality of keypoints and the second plurality of keypoints further includes:

generating a first keypoint graph corresponding to the first plurality of keypoints;

generating a first virtual centroid based on the first keypoint graph, the first virtual centroid defining a geometric center of the first plurality of keypoints;

generating a second keypoint graph corresponding to the second plurality of keypoints; and generating a second virtual centroid based on the second keypoint graph, the second virtual centroid defining a geometric center of the second plurality of keypoints.

14. The system of claim 11, wherein generating the first tool-level graph includes assigning a weight, using the attention model, to each keypoint of the first plurality of keypoints.

15. The system of claim 11, wherein generating the output image includes determining, using the attention model, which output location for each keypoint in the first plurality of keypoints in the first output image most closely corresponds to a historical trajectory of each keypoint in the first plurality of keypoints.

16. A non-transitory machine-readable medium having stored thereon machine-readable instructions executable to cause a machine to perform operations that predict movement of a first plurality of keypoints of a first surgical instrument, the operations comprising:

receiving, at a neural network model:

a first location of each keypoint of the first plurality of keypoints of the first surgical instrument; and a first location of each keypoint of a second plurality of keypoints of a second surgical instrument;

determining, using the neural network model, a trajectory for each keypoint of the first plurality of keypoints and the second plurality of keypoints by:

generating, using an attention model of the neural network model, a first tool-level graph indicating a spatial-temporal relationship between the first plurality of keypoints of the first surgical instrument;

generating, using the attention model of the neural network model, a second tool-level graph indicating a spatial-temporal relationship between the second plurality of keypoints of the second surgical instrument; and generating a scene-level graph based on the first and second tool-level graphs, the scene-level graph indicating a spatial-temporal relationship between the first plurality of keypoints and the second plurality of keypoints; and generating, using the neural network model, an output image based on the determined trajectory for each keypoint of the first plurality of keypoints and the second plurality of keypoints, the output image including:

an output location of each keypoint of the first plurality of keypoints annotated on an output image of the first surgical instrument; and an output location of each keypoint of the second plurality of keypoints annotated on an output image of the second surgical instrument.

17. The non-transitory machine-readable medium of claim 16, wherein determining the trajectory for each keypoint of the first plurality of keypoints and the second plurality of keypoints further includes:

extracting, using the neural network model, a first temporal correlation between each keypoint of the first plurality of keypoints along a temporal dimension of the attention model; and extracting, using the neural network model, a second temporal correlation between each keypoint of the second plurality of keypoints along the temporal dimension of the attention model.

18. The non-transitory machine-readable medium of claim 16, wherein determining the trajectory for each keypoint of the first plurality of keypoints and the second plurality of keypoints further includes:

generating a first keypoint graph corresponding to the first plurality of keypoints;

generating a first virtual centroid based on the first keypoint graph, the first virtual centroid defining a geometric center of the first plurality of keypoints, wherein the first tool-level graph is generated based on the first virtual centroid;

generating a second keypoint graph corresponding to the second plurality of keypoints; and generating a second virtual centroid based on the second keypoint graph, the second virtual centroid defining a geometric center of the second plurality of keypoints, wherein the second tool-level graph is generated based on the second virtual centroid.

19. The non-transitory machine-readable medium of claim 16, wherein generating the first tool-level graph includes assigning a weight, using the attention model, to each keypoint of the first plurality of keypoints.

20. The non-transitory machine-readable medium of claim 16, wherein generating the output image includes determining, using the attention model, which output location for each keypoint in the first plurality of keypoints in the first output image most closely corresponds to a historical trajectory of each keypoint in the first plurality of keypoints.

* * * * *